United States Patent [19]

Lotsof

[11] Patent Number: 4,587,243

[45] Date of Patent: May 6, 1986

[54] RAPID METHOD FOR INTERRUPTING THE COCAINE AND AMPHETAMINE ABUSE SYNDROME

[76] Inventor: Howard S. Lotsof, 330 Stanley Ave., Staten Island, N.Y. 10301

[21] Appl. No.: 754,836

[22] Filed: Jul. 15, 1985

[51] Int. Cl.$^4$ ............................................. A61K 31/55
[52] U.S. Cl. .................................................. 514/214
[58] Field of Search ................................ 514/210, 214

[56] References Cited

U.S. PATENT DOCUMENTS 4,499,096  2/1985  Lotsof .................................. 514/214

Primary Examiner—Stanley J. Friedman
Attorney, Agent, or Firm—Howard C. Miskin

[57] ABSTRACT

The administration to a cocaine or amphetamine abuser of ibogaine, ibogaine HCl or other non toxic salts of ibogaine, an alkaloid of the family apocynaceae, has been discovered to unexpectedly interrupt the physiological and psychological aspect of the cocaine and/or amphetamine abuse syndrome. A single treatment was effective for about 6 months, and a series of 4 treatments was effective for approximately 3 years. The treatments consisted of the oral administration of ibogaine or its salts in dosage ranges of 6 mg/kg to 19 mg/kg. The minimum effective dose was 400 mgs and dosage increases above 1000 mgs were found to be unnecessary. Treatments were effective in 100% of the cases.

9 Claims, No Drawings

RAPID METHOD FOR INTERRUPTING THE COCAINE AND AMPHETAMINE ABUSE SYNDROME

BACKGROUND OF THE INVENTION

The present invention relates generally to improvements in the treatment of cocaine and/or amphetamine abuse and it relates particularly to an improved method for interrupting the physiological and psychological aspects of the cocaine and/or amphetamine habituation.

Treatment proqedures heretofore employed or proposed for the interruption of the cocaine and/or amphetamine habituation syndrome, including the administration of antidepressants and/or tranquilizers, have been generally ineffective.

HISTORICAL BACKGROUND

Ibogaine is one of at least 12 alkoloids found in the Tabernanthe iboga shrub of West Africa. The indigenous peoples have used the drug as a ritual, ordeal or initiation potion in large dosages as a stimulant in smaller doses. One of the first European references to the drug was made by Professor Baillon on the Mar. 6th, 1889 session of the Linnaen Society in Paris during which he described samples obtained by Griffon de Bellay from Gabon and the French Congo.

Early isolation, and identification of ibogaine was accomplished by Dybowski and Landrin (Compt. rend. ac. sc. 133:748, 1901); Haller and Heckel (ibid. 133:850); Lambert and Heckel (ibid. 133:1236) and Landrin (Bull. sc. pharm. 11:1905).

Interest in the drug seemed to lie fallow until it was picked up by Raymond-Hamet and his associates Rothlin, E. and Raymon-Hamet published the "Effect of Ibogaine on the Isolated Rabbit Uterus" in 1938 (Compt. rend. soc. biol. 127:592-4). Raymond-Hamet continued to study the drug for a period of 22 years. He singularly published 9 papers: Pharmacological Action of Ibogaine (Arch. intern. pharmacodynamie, 63:27-39, 1939), Two Physiological Properties Common to Ibogaine And Cocaine (Compt. rend. soc. biol. 133:426-9, 1940), Ibogaine And Aphedrine (Ibid. 134:541-4, 1940), Difference Between Physiological Action of Ibogaine And That of Cocaine (Ibid. 211:285-8, 1940), Mediate And Intermediate Effects Of Ibogaine On The Intestine (Compt. rend. soc. biol. 135 176-79, 1941), Pharmacologic Antagonism Of Ibogaine (Compt. rend. 212: 768-771, 1941), Some Color Reactions Of Ibogaine (Bull. soc. chim. Biol., 25: 205-10, 1943), Sympathicosthenic Action Of Ibogaine On The Vessels Of the Dog's Paw (Compt. rend 223: 757-58, 1946), and Interpretation Of The Ultraviolet Absorption Curves Of Ibogaine And Tabernanthine (Ibid. 229: 1359-61, 1949).

Vincent, D. began his work on ibogaine by a collaboration with Sero, I.: Inhibiting Action Of Tabernanthe Iboga On Serum Cholinesterase (Compt. rend, Soc. Biol. 136: 612-14, 1942). Vincent participated in the publication of five other papers: The Ultraviolet Absorption Spectrum Of Ibogaine (Brustier, B., Vincent, D., & Sero, I., (Compt. rend., 216: 909-11, 1943), Detection of Cholinesterase Inhibiting Alkaloids (Vincent, D. & Beaujard, P., Ann. pharm. franc. 3: 22-26, 1945), The Cholinesterase Of The Pancreas: Its Behavior In the Presence Of Some Inhibitors In Comparison With The Cholinesterases of Serum And Brain (Vincent, D. & Lagreu, P., Bull. soc. chim. biol. 31: 1043-45, 1949); and two papers, which he and Raymond-Hamet worked on together: Action Of Some Sympathicosthenic Alkaloids On the Cholinesterases (Compt. rend. soc. biol., 150: 1384-1386, 1956) and On Some Pharmacological Effects Of Three Alkaloids Of Tabernanthe Iboga, Baillon: Ibogaine, Iboluteine And Tabernanthine (Compt. rend. soc. biol., 154: 2223-2227, 1960).

The structure of ibogaine was investigated by Dickel et al. (J.A.C.S. 80, 123, 1958). The first total synthesis was cited by Buchi et al. (J.A.C.S. 87, 2073, 1965) and (J.A.C.S. 88, 3099, 1966).

In 1956 Salmoiraghi and Page elucidated ibogaine's relations to serotonin (J. Pharm & expt. ther. 120 (1), 20-25, 1957.9). About the same time J. A. Schneider published three important papers. The first, Potentiation Action Of Ibogaine On Morphine Analgesia was done in collaboration with Marie McArthur (Experiential 12: 323-324, 1956). The second was Neuropharmacological Studies of Ibogaine: An Indole Alkaloid With Central-Stimulant Properties (Schneider, J. A. & Sigg, E. B., Annals of N.Y. acad, of sciences, Vol 66: 765-776, 1957) and third was An Analysis Of the Cardiovascular Action Of Ibogaine HCL (Schneider, J. A. & Rinehard, R. K., Arch. int. pharmacodyn., 110: 92-102, 1957).

Ibogaine's stimulant properties were further investigated by Chen and Bohner in A Study Of Central Nervous System Stimulants (J. Pharm. & Expt. Ther., 123 (3): 212-215, 1958). Gerson and Lang published A Psychological Study Of Some Indole Alkaloids (Arch. intern. pharmacodynamie, 135: 31-56, 1962).

R. D. Bunag, in 1963, evaluated certain aspects of the relationship between ibogaine and Substance P (Bunag, R. D.; Walaszek, E. J. The Cardiovascular Effects of Substance P in the Chicken Ann. N.Y. Acad. Sci. 104, Part 1, 437-48, 1963.)

In 1969, Claudio Naranjo reported on the effects of both ibogaine and harmine on human subjects in his paper: Psychotherapeutic Possibilities Of New Fantasy-Enhancing Drug (Clinical Toxicology, 2 (2): 209-224, June 1969).

Dhahir, H. I., as his 1971 doctoral thesis, published A Comparative Study Of The Toxicity Of Ibogaine And Serotonin (University Microfilm International 71-25-341, Ann Arbor, Mich.). The paper gives an overview of much of the work accomplished with ibogaine.

Additionally studies of interest include: The Effects Of Some Hallucinogens On Aggressiveness Of Mice And Rats (Kostowski et al., Pharmacology 7: 259-263, 1972), Cerebral Pharmacokinetics Of Tremor-Producing Harmala And Iboga Alkaloids (Zetler et al., Pharmacology 7 (4): 237-248, 1972), High Affinity 3H-Serotonin Binding To Caudate: Inhibition By Hallucinogenis And Serotonergic Drugs (Whitaker, P. & Seeman, P., Psychopharmacology 59: 1-5, 1978, Biochemistry), Selective Labeling Of Serotonin Receptors by d-(3H) Lysergic Acid Diethylamide In Calf Caudate (Proc. natl. acad. sci., USA, Vol. 75, No. 12, 5783-5787, Dec. 1978, Biochemistry) and A Common Mechanism Of Lysergic Acid, Indolealkylamine And Phenthylamine Hallucinogens: Serotonergic mediation of Behavioral Effects In Rats (Sloviter, Robert et al, J. Pharm. & Expt. Ther., 214 (2): 231-238, 1980).

SUMMARY OF THE INVENTION

It is a principal object of the present invention to provide an improved method for the treatment of cocaine and/or amphetamine abuse.

Another object of the present invention is to provide an improved method for interrupting the physiological and psychological aspect of the cocaine and/or amphetamine habituation.

Still another object of the present invention is to provide a method of the above nature characterized by its high degree of success, the absence of the great pain and discomfort accompanying earlier treatments, the ease and convenience of application the absent of undesirable or persistent side effects and the persistent effectiveness of the treatment.

The above and other object of the present invention will become apparent from a reading of the following description which sets forth preferred embodiments thereof.

A feature of the present invention is based on the discovery that an alkaloid of the family Apocynaceae and its therapeutically active derivatives and salts, particularly, ibogaine and its therapeutically active, non-toxic derivatives and salts for example, ibogaine hydrochloride and other non-toxic salts of ibogaine, possess the unexpected unique ability to disrupt the cocaine and/or amphetamine habituation syndrome. Examples of other salts of ibogaine which may be used are ibogaine hydrobromide, and any other non-toxic salt of ibogaine.

For the purpose of definition, the cocaine and/or amphetamine abuse syndrome is meant to consist of all the symptomology demonstrated by users in their use of and search of cocaine or amphetamine. The interruption of the syndrome was accomplished in three out of three (100%) of the tests subjects who were habituated to amphetamine or cocaine. None of the test subjects were seeking to terminate their use, and all three enjoyed stimulant use.

A single treatment with ibogaine or ibogaine HCL of doses ranging from 6 mg/kg to 19 mg/kg administered orally, disrupted the subject's use of cocaine and/or amphetamine for about six months.

A treatment lasts about thirty hours during which time ibogaine exerts a stimulant effect. Apparently, an abreactive process is involved during ibogaine therapy but is not noticeable until the patient wakes from natural sleep occurring after primary and secondary effects of ibogaine are diminished. When effective, ibogaine left the abuser with no desire to use stimulants and no noticeable signs of physical or psychological withdrawal. Subjects appeared relaxed, coherent, with a sense of direction and feelings of confidence.

Ibogaine was one of five substances we studied. The other four—mescaline, psilocybin, LSD and DMT though different in duration of action and intensity—have similar psychotrophic effects that are well documented and will not be discussed here. Ibogaine, unlike the others, is not a euphoriant hallucinogen and did not leave the subjects open to swells of emotion. While under the influence of ibogaine, emotional responses to traumatic repressed thoughts and feelings appeared to be negated.

Another effect of ibogaine administration that was found interesting was that even after twenty-six to thirty hours of wakefulness, subjects slept three to four hours and awoke fully rested. This pattern continued, diminishing slowly, over a three to four month period.

The effects of oral administration of ibogaine are first noticed in fifteen to twenty minutes. Initially, a numbing of the skin is accompanied by an auditory buzzing or oscillating sound. Within twenty-five to thirty-five minutes the auditory transcends across the sensory mechanisms to include the visual: objects appear to vibrate with great intensity. It is at this time that the dream enhancement or hallucinatory effects begin. In many cases an acute stage of nausea follows the hallucinatory phase. The visions end abruptly and the numbness of the skin begins to abate.

This is followed by six to eight hours of a high energy state during which the subjects see "lightning" or flashes of light dance about them. Thoughts which seem to amplify the meaning of the visions seen during the primary phase of ibogaine intoxication continue during this period.

Between twenty-six and thirty-six hours, the level of stimulation diminishes and the test subject falls asleep.

Thus, three stages of ibogaine intoxication have been observed. First, an hallucinatory period lasting for three to four hours during which time the person receiving ibogaine manifests repressed material visually. Second, a high energy period accompanied by flashes of light, the appearance of a vibration to all objects, and the awareness of thoughts appropriate to the visual material seen by the subject. Third, a diminishing energy period free of vibration or light flashes and culminating in sleep.

In the administration of acceptable dosage forms, any one of a variety of preparations may be compounded, for example: capsules, tablets, pills, powder, solutions, etc. In addition to the active agent, there may be present additional substances used in the manufacture of pharmaceutical preparations such as binders, fillers and other inert ingredients.

DESCRIPTION OF THE PREFERRED EMBODIMENTS

The following examples are given merely by way of illustration and are not intended to limit the scope of the present invention.

EXAMPLE 1

Male, age 19, weight 143 lbs. The subject was using both cocaine and amphetamine. Cocaine use consisted of two to three grams of pharmaceutical grade cocaine HCl. The routes of administration were nasal, I.V. injection and smoking in combination with marijuana and hashish in cigarettes. Amphetamine use consisted of 300 mg to 500 mg per week, generally taken over a one or two day period. The principal forms of amphetamines used were d-amphetamine tannate, d-amphetamine sulfate and d-desoxyephedrine HCl. Drug use at the above levels has been consistent for two months.

All treatments were by oral ingestion in capsules. The first treatment consisted of 400 mg of ibogaine HCl. This curtailed amphetamine and cocaine use for six months at which time a series of treatments was administered.

Treatments within the series were spaced at seven day intervals. The first dose was 500 mg of ibogaine. The second was 500 mg plus 250 mg fifteen minutes later, the third was 600 mg and the final dose was 1000 mg.

The series was considered complete when the subject ceased to experience the hallucinatory stage and no longer desired to use additional ibogaine. This occurred upon administration of the third and fourth doses in the series, respectivley.

The subject remained amphetamine free for six months and cocaine free for eighteen months.

EXAMPLE 2

Male, age 20, weight 135 lbs. Subject was using two to four grams of d-desoxyephedrine HCl a week. The route of administration was I.V. injection. The general pattern of use consisted of three to four days of continuous use followed by a day or two of "crashing." After treatment with a single 500 mg dose of ibogaine the subject remained stimulant free for six months.

EXAMPLE 3

Female, age 23, weight 95 lbs. Cocaine use consisted of two to three grams of pharmaceutical grade cocaine HCl administered nasally or by I.V. injection. Amphetamine use consisted of 500 mg to 1000 mg of d-desoxyephedrine HCl or de-amphetamine sulfate taken orally. The above figures represent weekly totals. A single dose of 500 mg of ibogaine curtailed cocaine and amphetamine use for six months at which time we lost contact with this subject.

MODE OF ACTION

There are a number of mechanisms and relationships of action by which ibogaine may interupt the amphetamine and/or cocaine abuse syndrome. These include memory coding by RNA and protein, immune mechanisms, neurohormonal adaptations, involvement in systems including catecholamines, acetylcholine, serotonin, adrenergis compounds, hypothalmic-pituitary neuro-hormones, opiate receptor outside the CNS as well as adaptations taking place outside the central nervous system. The mode of action may also include structure-activity relationships, receptor within the brain or other binding sites, psychological causes, systems involving endorphins, metabolic imbalances, prevention of access of drugs to the site of action, or occupation and saturation of receptor sites as well as interaction with systems involving Substance P and mechanisms controlling spindling.

While the exact mechanism or mechanisms of action by which ibogaine interrupts the cocaine and/or amphetamine abuse syndrome is not clear, it is known that it functions by interaction with one or more of the above systems. It is not intended, however, that the present invention be limited to any particular theory or mechanism of action.

The advantage of this invention is that it allows for the rapid interruption of physiological and psychological withdrawal and the elimination of the subject's desire to use stimulants for about six months. The invention itself is non-addicting, and in a series of treatments will remove its own potential for abuse.

While there have been described preferred embodiments of the present invention it is apparent that numerous alterations, omissions and additions may be made without departing from the spirit thereof.

I claim:

1. The method of treating cocaine and/or amphetamine abuse comprising internally administering to the abuser a composition including ibogaine or a therapeutically active compound thereof or a mixture thereof.

2. The method of claim 1 wherein said composition is norally administered.

3. The method of claim 1 or 2 wherein said compound includes a non-toxic salt of ibogaine.

4. The method of claim 1 or 2 wherein there is administered a dosage of said composition containing ibogaine or one or more non-toxic salts thereof or a mixture thereof of between 6 mg and 19 mg per kg weight of the abuser.

5. The method of claim 3 or 4 wherein the administered dosage of said composition contains ibogaine or its non-toxic salt or a mixture thereof of between 400 mg and 1000 mg.

6. The method of claim 3, 4 or 5 wherein a plurality of doses of said composition are administered, the administration of successive doses being separated by a plurality of days.

7. The method of claim 3 wherein said ibogaine is in the form of the hydrochloride or hydrobromide salt thereof.

8. The method of claim 4 wherein said dosage is in capsule, tablet, pill, powder or solution form.

9. The method of claim 4 wherein said dosage is admixed with binders, fillers or other inert ingredients.

* * * * *